United States Patent
Radwanski et al.

(10) Patent No.: US 10,391,213 B2
(45) Date of Patent: Aug. 27, 2019

(54) SYSTEMS AND METHODS FOR THERAPEUTIC PLATELET DEPLETION

(71) Applicant: Fenwal, Inc., Lake Zurich, IL (US)

(72) Inventors: Katherine N. Radwanski, Highland Park, IL (US); Kyungyoon Min, Kildeer, IL (US); Zahra R. Ali, Chicago, IL (US)

(73) Assignee: Fenwal, Inc., Lake Zurich, IL (US)

(*) Notice: Subject to any disclaimer, the term of this patent is extended or adjusted under 35 U.S.C. 154(b) by 0 days.

(21) Appl. No.: 15/615,962

(22) Filed: Jun. 7, 2017

(65) Prior Publication Data

US 2017/0354770 A1    Dec. 14, 2017

Related U.S. Application Data

(60) Provisional application No. 62/347,125, filed on Jun. 8, 2016.

(51) Int. Cl.
*A61M 1/02* (2006.01)
*A61M 1/30* (2006.01)
(Continued)

(52) U.S. Cl.
CPC .............. *A61M 1/02* (2013.01); *A61M 1/029* (2013.01); *A61M 1/30* (2013.01); *A61M 1/304* (2014.02);
(Continued)

(58) Field of Classification Search
CPC .......... A61M 1/02; A61M 1/304; A61M 1/38; A61M 1/3693; A61M 1/3696;
(Continued)

(56) References Cited

U.S. PATENT DOCUMENTS 4,216,770 A * 8/1980 Cullis ................. A61M 1/3693
                                                          424/611
5,316,667 A    5/1994 Brown et al.
(Continued)

FOREIGN PATENT DOCUMENTS

WO    WO 01/28652 A1    4/2001
WO    WO 2012/139017    10/2012
WO    WO 2013/048984 A1    4/2013

OTHER PUBLICATIONS

Hernandez-Boluda, J., et al. "Target hematologic values in the management of essential thrmobocythemia and polycythemia vera", European Journal of Haematology, 94, pp. 4-11 (2015). Epub May 29, 2014.*
(Continued)

*Primary Examiner* — Benjamin L Lebron
(74) *Attorney, Agent, or Firm* — Cook Alex Ltd.

(57) ABSTRACT

Systems and methods are provided for depleting platelets from blood. The system includes a multi-stage blood separation chamber in which blood is separated into red blood cells and platelet-rich plasma. The platelet-rich plasma is conveyed from a first stage of the chamber to a second stage, where it is separated into platelets and platelet-poor plasma. The platelet-poor plasma is conveyed out of the chamber while the platelets are allowed to accumulate in the second stage of the chamber. When a controller of the system has determined that the maximum chamber capacity of platelets has been accumulated in the second stage of the chamber, the platelets are conveyed out of the chamber to a waste container. The cycle of separating blood into its components, accumulating platelets in the chamber, and then flushing the platelets from the chamber is repeated until a target platelet concentration of the blood is achieved.

2 Claims, 10 Drawing Sheets

(51) Int. Cl.
*A61M 1/36* (2006.01)
*A61M 1/38* (2006.01)
*B04B 5/04* (2006.01)
*B04B 7/00* (2006.01)
*B04B 11/06* (2006.01)
*B01D 61/14* (2006.01)

(52) U.S. Cl.
CPC ........ *A61M 1/3633* (2013.01); *A61M 1/3693* (2013.01); *A61M 1/3696* (2014.02); *A61M 1/38* (2013.01); *A61M 1/382* (2013.01); *A61M 1/385* (2013.01); *B04B 5/0442* (2013.01); *B04B 7/00* (2013.01); *B04B 11/06* (2013.01); *A61M 1/0209* (2013.01); *A61M 2202/0071* (2013.01); *A61M 2202/0427* (2013.01); *A61M 2205/12* (2013.01); *A61M 2205/33* (2013.01); *A61M 2205/3306* (2013.01); *A61M 2205/50* (2013.01); *B01D 61/14* (2013.01)

(58) Field of Classification Search
CPC ...... A61M 1/029; A61M 1/385; A61M 1/382; A61M 1/0209; A61M 2202/0427; A61M 2205/12; A61M 1/30; A61M 1/3633; A61M 2202/0071; A61M 2205/33; A61M 2205/3306; A61M 2205/50; B01D 61/14; B04B 7/08; B04B 5/0442; B04B 2005/045; B04B 7/00; B04B 11/06
See application file for complete search history.

(56) References Cited

U.S. PATENT DOCUMENTS

| | | | |
|---|---|---|---|
| 5,614,106 A * | 3/1997 | Payrat | A61M 1/3672 210/206 |
| 5,632,893 A | 5/1997 | Brown et al. | |
| 5,649,903 A | 7/1997 | Deniega et al. | |
| 5,759,413 A | 6/1998 | Brown | |
| 5,868,696 A | 2/1999 | Giesler et al. | |
| 5,980,757 A | 11/1999 | Brown et al. | |
| 6,312,607 B1 | 11/2001 | Brown et al. | |
| 6,565,806 B1 * | 5/2003 | Grimm | A61M 1/3672 422/44 |
| 6,743,192 B1 * | 6/2004 | Sakota | A61M 1/3693 210/195.1 |
| 2002/0032398 A1 | 3/2002 | Steele | |
| 2002/0062100 A1 * | 5/2002 | Pierce | A61M 1/02 604/6.01 |
| 2006/0161092 A1 | 7/2006 | Westberg | |
| 2007/0213191 A1 * | 9/2007 | Chammas | B04B 5/0442 494/41 |
| 2008/0050275 A1 | 2/2008 | Bischof | |
| 2009/0215602 A1 * | 8/2009 | Min | A61M 1/3693 494/4 |
| 2009/0259162 A1 | 10/2009 | Ohashi | |
| 2010/0234788 A1 | 9/2010 | Pages | |
| 2012/0010062 A1 * | 1/2012 | Fletcher | A61M 1/3693 494/10 |
| 2012/0225419 A1 | 9/2012 | Min et al. | |
| 2013/0196840 A1 * | 8/2013 | Pieper | B04B 7/08 494/37 |
| 2013/0280342 A1 | 10/2013 | Pages | |
| 2014/0043930 A1 | 2/2014 | Belt et al. | |
| 2014/0045668 A1 | 2/2014 | Case et al. | |
| 2015/0056602 A1 | 2/2015 | Radwanski et al. | |

OTHER PUBLICATIONS

Extended European Search Report for Application No. EP17174699.3 dated Oct. 25, 2017.

K. Janetzko et al.: "Efficiency of the Cell Separator AMICUS for Platelet Depletion in the Treatment of Essential Thrombocythemia", Jan. 1, 2001 (Jan. 1, 2001), XP055416446, Retrieved from the Internet: URL: http//onlinelibrary.wiley.com/store/10.1002/jca.1007/asset/1007_ftp.pdf?v=1&t=i8vlwuvz&s= 6e687d4ad42dd157b1008c9bef42b981daf4d062 [retrieved on Oct. 17, 2017].

* cited by examiner

PRIOR ART

SYSTEMS AND METHODS FOR THERAPEUTIC PLATELET DEPLETION

CROSS REFERENCE TO RELATED APPLICATIONS

This application claims the benefit of and priority of U.S. Provisional Patent Application Ser. No. 62/347,125, filed Jun. 8, 2016, the contents of which are incorporated by reference herein.

BACKGROUND

Field of the Disclosure

The invention relates to blood separation systems and methods. More particularly, the invention relates to systems and methods for depleting platelets from blood during a blood treatment procedure.

Description of Related Art

Various blood processing systems make it possible to separate blood into two or more constituent parts, which may be useful for donation purposes and for treatment of individuals with potentially detrimental or harmful blood conditions or disorders.

When such systems are used for blood component donation, whole blood is typically drawn from a donor, the particular blood component or constituent is removed and collected, and the remaining blood constituents are returned to the donor. By thus removing only particular constituents, potentially less time is needed for the donor's body to return to normal, and donations can be made at more frequent intervals than when whole blood is collected. This increases the overall supply of blood constituents, such as plasma and platelets, made available for health care.

Similar procedures may be performed to treat individuals with potentially detrimental or harmful blood conditions or disorders. For example, thrombocytosis is a blood condition in which too many platelets are produced by the body and may be caused by either a bone marrow disorder (which may be referred to as "essential thrombocytosis") or, more commonly, by some other underlying cause (e.g., a major surgery, such as a splenectomy), in which case the condition may be referred to as "reactive thrombocytosis." Depending on the severity of the condition, thrombocytosis may lead to potentially life-threatening thrombotic events, such as heart attacks and embolisms. Thus, in cases of extreme thrombocytosis, the health of a patient may be improved by removing a portion of the platelets of their blood.

Whole blood is typically separated into its constituents through centrifugation. This requires that the whole blood be passed through a centrifuge after it is withdrawn from, and before it is returned to, the source. To avoid contamination of the blood and possible infection of the source (if the source is a living donor or patient), the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable separation chamber of the fluid processing assembly during a collection or treatment procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber of the fluid processing assembly. The lighter (lower specific gravity) components, such as plasma, migrate toward the inner or "low-G" wall of the separation chamber. Various ones of these components can be selectively removed from the whole blood by forming appropriately located channeling seals or barriers and outlet ports in the separation chamber of the fluid processing assembly.

According to one conventional approach to therapeutic platelet depletion, blood in a single-stage separation chamber is separated into red blood cells, plasma, and a "buffy coat," which contains blood constituents having an intermediate specific gravity, including platelets and white blood cells. The buffy coat is continuously removed from the separation chamber and conveyed to a waste container, while the separated plasma and red blood cells are returned to the blood source. While such a procedure has proven to be effective in treating extreme thrombocytosis, there are some potential drawbacks, as the buffy coat includes not only the targeted platelets, but also white blood cells and smaller red blood cells. Additionally, due to this being a continuous process, the waste volume generated may be larger than desired (e.g., on the order of approximately 1000 mL per procedure), which requires costly replacement fluid to be conveyed to the blood source to maintain fluid balance.

Accordingly, it would be advantageous to provide systems and methods that are capable of depleting platelets from blood without the potential drawbacks associated with the conventional approach.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for depleting platelets from the blood of a blood source. The method includes executing a cycle in which blood is conveyed into a first stage of a blood separation chamber and separated into platelet-rich plasma and red blood cells. At least a portion of the platelet-rich plasma is conveyed from the first stage into a second stage of the blood separation chamber and separated into platelets and platelet-poor plasma. At least a portion of the platelet-poor plasma is conveyed out of the second stage of the blood separation chamber while the platelets are allowed to accumulate in the second stage. When it has been determined that a maximum chamber capacity of platelets has accumulated in the second stage of the blood separation chamber, the cycle is ended by conveying the accumulated platelets out of the second stage.

In another aspect, there is provided a blood separation device. The device includes a centrifuge configured to receive a blood separation chamber, a plurality of pumps, and a controller. The controller is programmed to execute a cycle in which it commands at least one of the pumps to convey blood from a blood source into a first stage of a blood separation chamber. The controller also commands the centrifuge to rotate the blood separation chamber to separate the blood in the first stage of the blood separation chamber into platelet-rich plasma and red blood cells. The controller commands at least one of the pumps to convey at least a portion of the platelet-rich plasma into a second stage of the blood separation chamber in which the rotation of the centrifuge causes the platelet-rich plasma to separate into platelets and platelet-poor plasma. Finally, as part of the cycle, the controller commands at least one of the pumps to convey at least a portion of the platelet-poor plasma out of the second stage of the blood separation chamber while allowing the platelets to accumulate in the second stage. The controller is further programmed to determine that a maximum chamber capacity of platelets has accumulated in the second stage of the blood separation chamber and end the cycle by commanding at least one of the pumps to convey the accumulated platelets out of the second stage.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Components of the Blood Processing System

Figure 1:
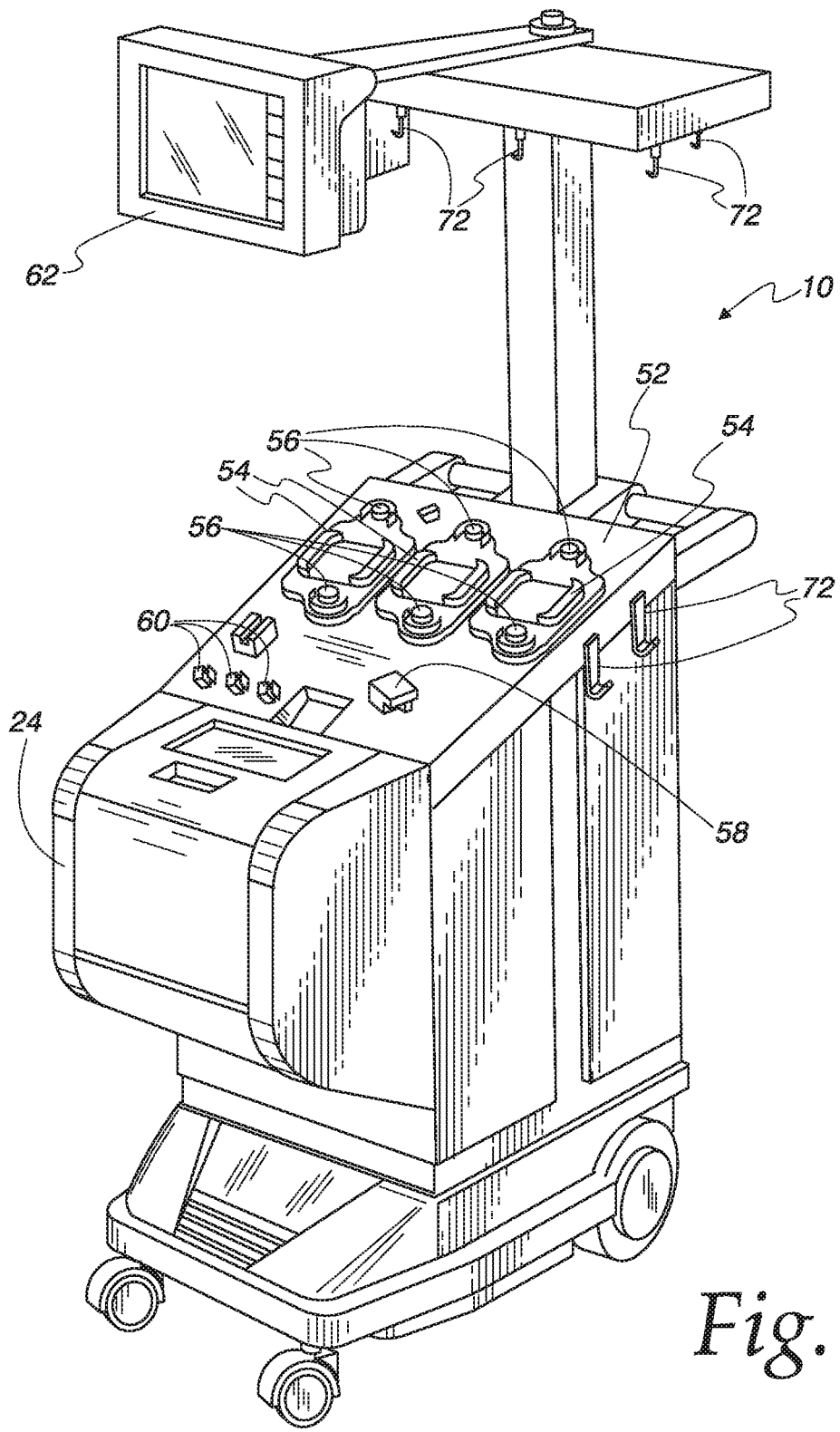
FIG. 1 is a is a perspective view of an exemplary blood separation device employing aspects of the present disclosure.

FIG. 1 shows an exemplary centrifugal blood separation device 10 that may be used in combination with a disposable fluid flow circuit 12 (FIG. 2) to comprise a blood processing system (FIGS. 3 and 4) for practicing the platelet depletion principles of the present disclosure. The illustrated blood separation device 10 is currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The device 10 can be used for processing various fluids, but is particularly well suited for processing whole blood, blood components, or other suspensions of biological cellular materials. While therapeutic platelet depletion will be described herein with reference to one particular device 10, it should be understood that these techniques may be employed with other blood separation devices without departing from the scope of the present disclosure.

The device 10 includes a centrifuge 14 (FIGS. 3 and 4) used to centrifugally separate blood components. The device 10 may be programmed to separate blood into a variety of components (e.g., platelet-rich plasma and red cells), which may include being programmable to execute a therapeutic platelet depletion, in which the centrifuge 14 separates whole blood into platelet-rich plasma and red blood cells and then separates the platelet-rich plasma into platelet-poor plasma and platelets or platelet concentrate, as will be described in greater detail.

Figure 3:
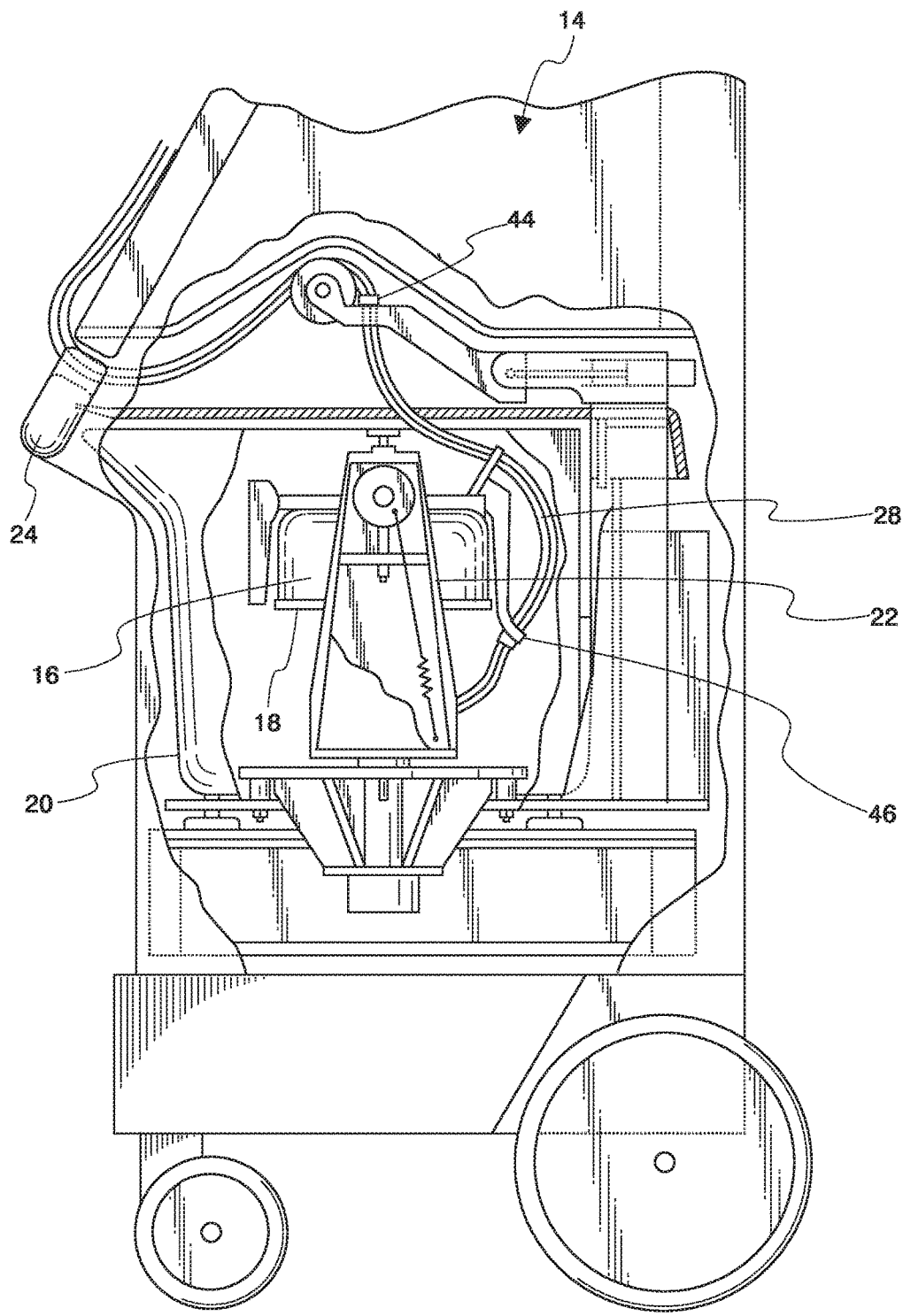
FIG. 3 is a side elevation view, with portions broken away and in section, of the blood separation device of FIG. 1, with a centrifuge bowl and spool of the device being shown in their operating position and with the fluid flow circuit of FIG. 2 mounted thereon.
Figure 4:
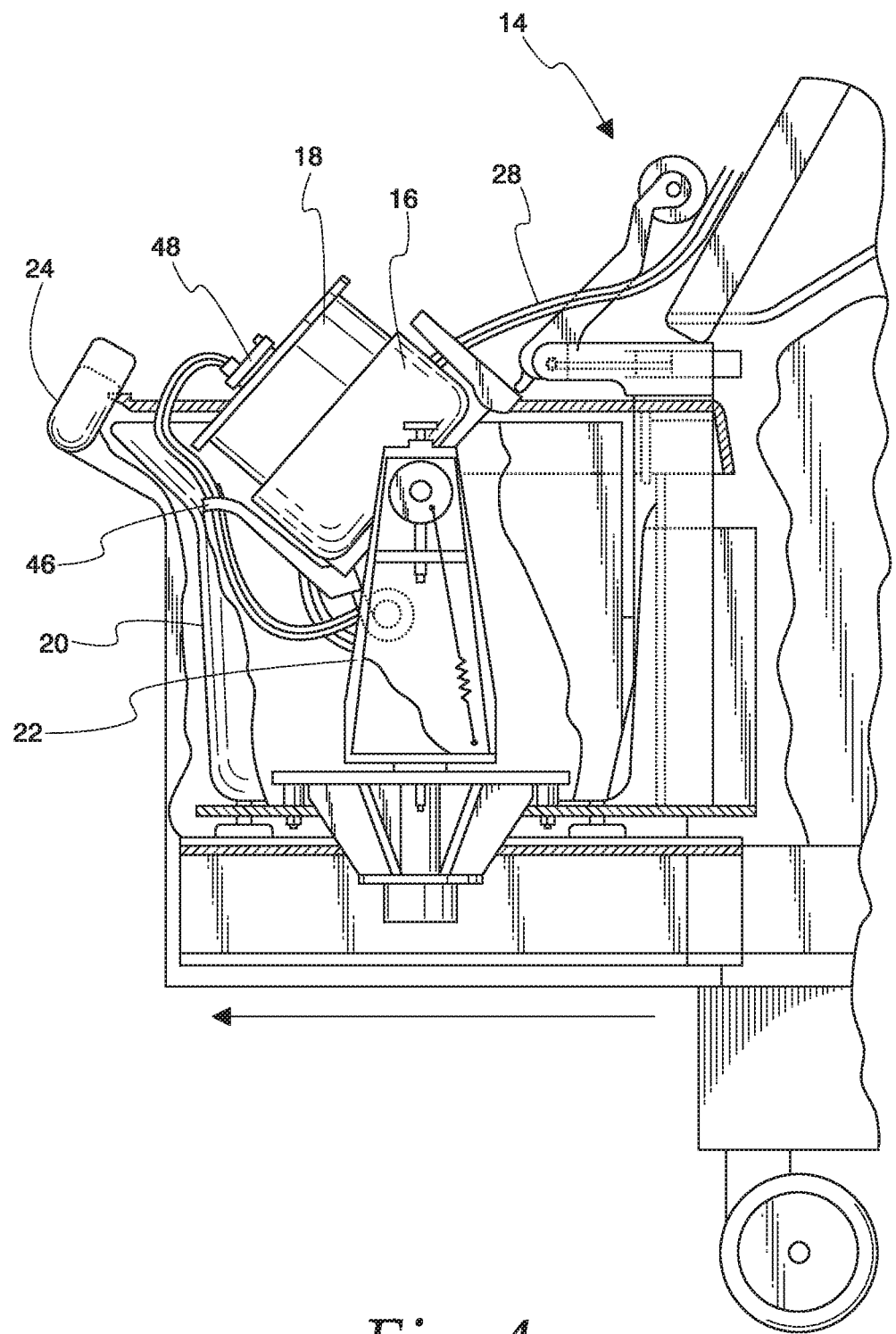
FIG. 4 is a side elevation view, with portions broken away and in section, of the device shown in FIG. 1, with the bowl and spool shown in an upright position for receiving a blood separation chamber of the fluid flow circuit of FIG. 2.

The illustrated centrifuge 14 is of the type shown in U.S. Pat. No. 5,316,667, which is hereby incorporated herein by reference. The centrifuge comprises a bowl 16 and a spool 18, which are received within a bucket or enclosure 20. The bowl 16 and spool 18 are pivoted on a yoke 22 between an operating position (FIG. 3) and a loading/unloading position (FIG. 4). The centrifuge 14 is housed within the bucket 20 in the interior of the separation device 10, so a door 24 may be provided to allow access to the centrifuge 14 for loading and unloading the fluid flow circuit 12. The door 24 remains closed during operation to protect and enclose the centrifuge 14.

When in the loading/unloading position, the spool 18 can be accessed by movement at least partially out of the bowl 16, as FIG. 4 shows. In this position, the operator wraps a flexible blood separation chamber 26 of the fluid flow circuit 12 (see FIG. 5) about the spool 18. Closure of the spool 18 and bowl 16 encloses the chamber 26 for processing. When closed, the spool 18 and bowl 16 are pivoted into the operating position of FIG. 3 for rotation about an axis.

Figure 5:
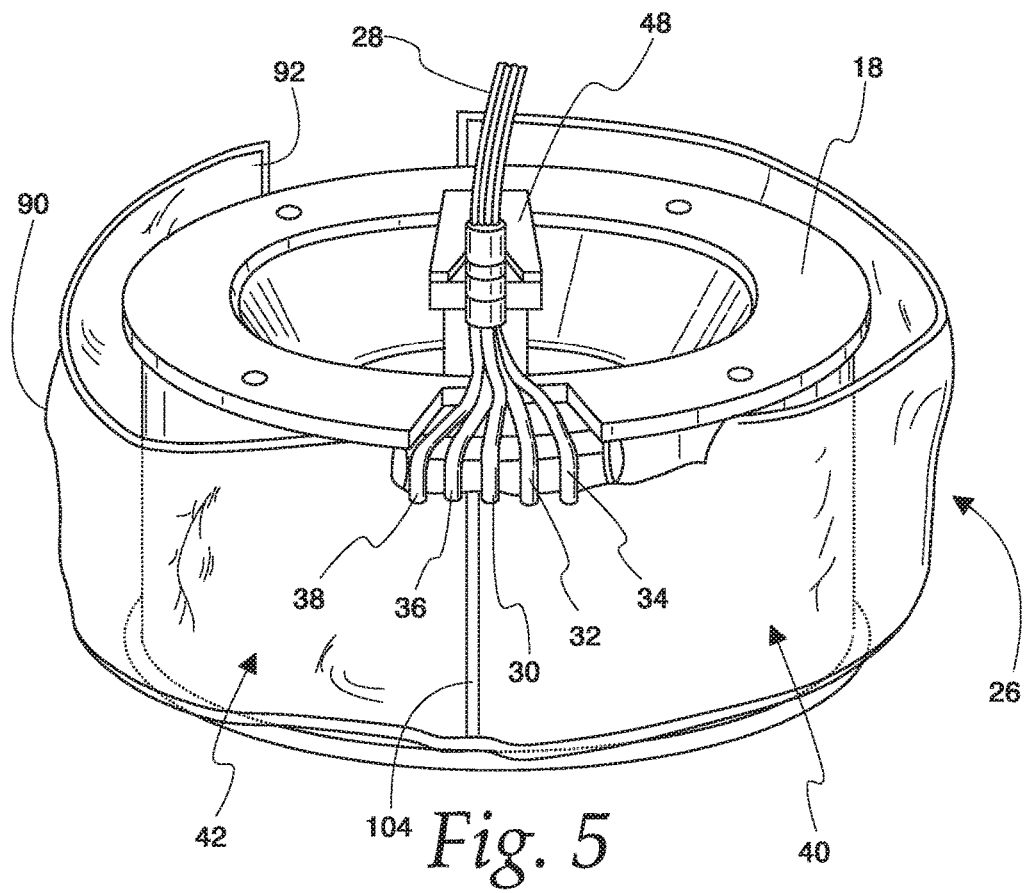
FIG. 5 is a top perspective view of the spool of the centrifuge shown in FIG. 4 in its upright position and carrying the blood separation chamber of the fluid flow circuit of FIG. 2.

While the chamber 26 of the flow circuit 12 is positioned within the centrifuge 14, other portions of the flow circuit 12 may remain outside of the bucket 20. In the illustrated embodiment, the various tubing connected to the blood separation chamber 26 are bundled in an umbilicus 28, which extends outside of the bucket 20 during use (FIG. 3). As best shown in FIG. 5, the umbilicus 28 of the flow circuit 12 may be attached to ports 30, 32, 34, 36, and 38 of the blood separation chamber 26 by individual tubing. The umbilicus 28 interconnects first and second stages 40 and 42 of the chamber 26 with each other and with the components of the flow circuit 12 positioned outside of the centrifuge 14 during use. As FIG. 3 shows, a non-rotating (zero omega) holder 44 holds the upper portion of the umbilicus 28 in a non-rotating position above the spool 18 and bowl 16. A holder 46 on the yoke 22 rotates the mid-portion of the umbilicus 28 at a first (one omega) speed about the suspended spool 18 and bowl 16. Another holder 48 (FIGS. 4 and 5) rotates the lower end of the umbilicus 28 at a second speed twice the one omega speed (the two omega speed), at which speed the spool 18 and bowl 16 also rotate. This known relative rotation of the umbilicus 28 keeps it untwisted, in this way avoiding the need for rotating seals.

The tubing of the umbilicus 28 may be connected to cassettes 50A, 50B, and 50C of the flow circuit 12 (FIG. 2), which are molded components that define a plurality of fluid flow segments that may be selectively placed into and out of fluid communication with each other via the operation of valve stations defined in the cassette. The illustrated flow circuit 12 includes three cassettes 50A, 50B, and 50C, which may be variously configured without departing from the scope of the present disclosure but, in one embodiment, are configured according to the description of U.S. Patent Application Publication No. 2014/0045668, which is hereby incorporated herein by reference. It is also within the scope of the present disclosure for the flow circuit 12 to include a different number of cassettes or for the flow circuit 12 to employ a non-cassette-based approach to fluid flow control.

A front panel 52 of the blood separation device 10 includes a plurality of cassette holders 54 (FIG. 1) to accommodate the cassettes 50A, 50B, and 50C of the flow circuit 12. Each cassette holder 54 receives and grips a different one of the cassettes 50A, 50B, 50C of the fluid flow circuit 12 along two opposed side edges in the desired operating position. Each cassette holder 54 includes a pair of peristaltic pump stations or pumps 56. When a cassette is gripped by the cassette holder 54, tubing loops 58 extending from the cassette (FIG. 2) make operative engagement with the pumps 56. The pumps 56 are operated under command of a system controller to cause fluid flow through the associated cassette.

Each cassette 50A, 50B, 50C may have a flexible diaphragm covering its underside, with the diaphragm being urged into intimate contact with a valve and sensor array or assembly of the associated cassette holder 54. The valve assembly acts in concert with valve stations and sensing stations of the associated cassette, with each valve station having a matching valve actuator and each sensing station having a matching pressure sensing transducer. The valve actuators and the pressure sensing transducers of each valve assembly are mutually arranged in the same layout as the valve stations and sensing stations on the underside of the associated cassette.

In one embodiment, each valve actuator includes an electrically actuated solenoid pin or piston, which is movable between an extended position and a retracted position. When in its extended position, the piston presses against the region of the diaphragm that overlies the associated valve station, which flexes the diaphragm into the associated valve station, thereby sealing the associated valve port defined by the cassette. This closes the valve station to liquid flow. When in its retracted position, the piston does not apply force against the diaphragm, such that the plastic memory of the diaphragm causes it to unseat from the valve port, thereby opening the valve station to liquid flow.

The pressure sensing transducers sense liquid pressures in the sensing stations of the cassettes. The sensed pressures may be transmitted to the controller of the separation device 10 as part of its overall system monitoring function.

The front panel 52 of the device 10 may include additional components, such as at least one optical line monitor 58. If provided, the optical line monitor 58 may receive a tubing or fluid flow conduit of the flow circuit 12 to optically monitor fluid flowing therethrough, as will be described in greater detail. The front panel 52 may also include various clamps 60 that receive a tubing or fluid flow conduit of the flow circuit 12 to selectively allow and prevent fluid flow through that conduit. Other components (e.g., air detectors and weigh scales) may also be incorporated into the front panel 52 of the device 10 without departing from the scope of the present disclosure.

A user interface screen 62 (e.g., a touchscreen) may be positioned above the front panel 52 (as in FIG. 1) or at some other location. The user interface screen 62 may allow an operator to interact with the system controller (e.g., a microprocessor) of the device 10 to provide instructions to the controller (e.g., to carry out a particular procedure), as well as providing information to the controller to be used during a procedure (e.g., a platelet pre-count of the blood of the blood source). The user interface screen 62 may provide the operator with instructions (e.g., to connect or disconnect the blood source from the flow circuit 12) and information (e.g., alerting the operator to a blockage in a fluid flow conduit of the flow circuit 12). In other embodiments, a differently configured user interface device (e.g., a computer terminal) may be employed in combination with the blood separation device 10.

Figure 2:
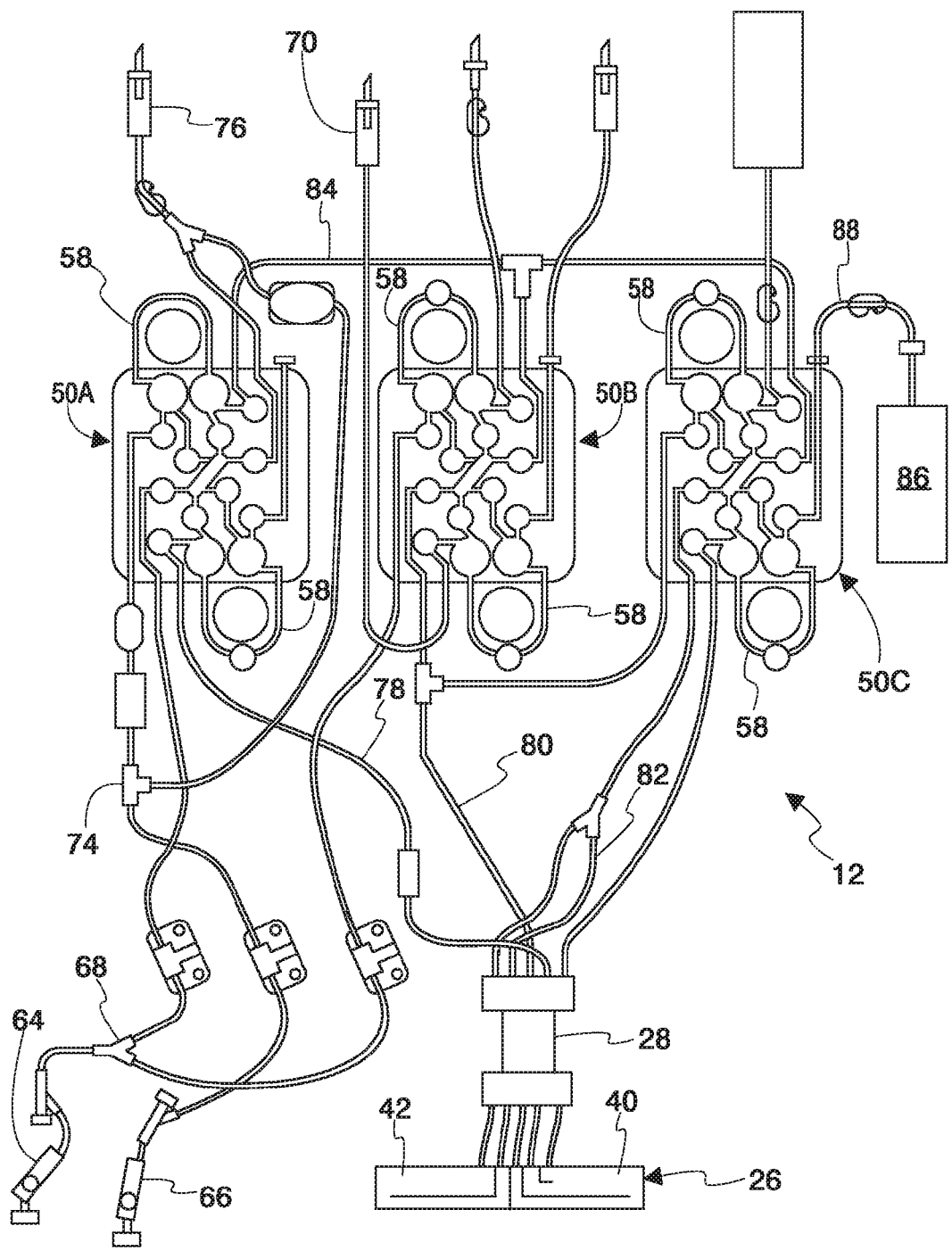
FIG. 2 is a diagrammatic view of an exemplary disposable fluid flow circuit that may be used in combination with the blood separation device of FIG. 1.

As noted, the various components of the fluid flow circuit 12 may be connected by flexible tubing or any other suitable fluid flow conduit. FIG. 2 illustrates an exemplary disposable fluid flow circuit 12 that may be used in combination with the blood separation device 10 of FIG. 1, but it should be understood that the fluid flow circuit 12 may be differently configured without departing from the scope of the present disclosure. For example, the illustrated flow circuit 12 is a "two needle" system, which includes a pair of blood source access devices 64 and 66 (e.g., phlebotomy needles) for fluidly connecting a blood source with the flow circuit 12, but it is within the scope of the present disclosure for the flow circuit to comprise a "single needle" system in which a single blood source access device (e.g., a phlebotomy needle) is used to both draw blood from a blood source and convey fluid to the blood source.

In the illustrated embodiment, the blood source access devices 64 and 66 are connected by tubing to a left cassette 50A. One of the blood source access devices 64 is used to draw blood from the blood source into the flow circuit 12 and is connected to the left cassette 50A by a y-connector 68. The other leg of the y-connector 68 is connected to tubing which leads to a middle cassette 50B. This tubing is connected, through the middle cassette 50A, to additional tubing, which includes a container access device 70 (e.g., a sharpened cannula or spike connector) for accessing the interior of an anticoagulant container (not illustrated). During a blood processing operation, anticoagulant from the anticoagulant container may be added to the blood from the blood source at the y-connector 68 prior to entering the left cassette 50A, such that the terms "blood" or "whole blood" as used herein should be understood as encompassing anticoagulated blood. The anticoagulant container (and any other container of the fluid flow circuit 12) may be suspended from a hanger or support 72 of the blood separation device 10. One or more of the supports 72 may be associated with a weigh scale, which monitors the change in weight of the container, thereby tracking the volume of fluid entering and exiting the container. Alternatively, other approaches (e.g., volumetric fluid flow monitoring) may be employed to determine the amount of fluid entering and exiting any of the containers of the fluid flow circuit 12.

The other blood source access device 66 may be used to deliver or return blood, a blood component, and/or some other replacement fluid to the blood source and is also connected to the left cassette 50A by a y-connector 74. The other leg of the y-connector 74 is connected to tubing connected at its other end to a container access device 76. Although not illustrated, the container access device 76 may be associated with a container having an amount of fluid (e.g., saline) to be used to prime the flow circuit 12, flush platelets from the blood separation chamber 26, and/or to be delivered to the blood source via the blood source access device 66.

The left cassette 50A also includes tubing or conduit 78 which is connected to the blood separation chamber 26 of the flow circuit 12 for flowing anticoagulated blood thereto. The blood separation chamber 26 separates the blood into its constituent parts (as will be described in greater detail herein) and returns the blood components to the flow circuit 12. In one embodiment, red blood cells are returned to the middle cassette 50B of the flow circuit 12 from the blood separation chamber 26 via tubing or conduit 80, while substantially cell-free plasma and platelets/platelet concentrate are alternately returned to a right cassette 50C of the flow circuit 12 from the blood separation chamber 26 via tubing or conduit 82. The red blood cells may be pumped to the left cassette 50A via tubing or conduit 84, where they are returned to the blood source. The platelet-poor plasma may be pumped back to the left cassette 50A via tubing 84 for return to the blood source with the red blood cells, while the platelets or platelet concentrate is pumped into a waste container 86 via a different tubing or conduit 88. This platelet depletion procedure will be described in greater detail herein. The destination of the platelets (and the other fluids passing through the cassettes) depends upon the actuation of the various valve stations of the cassettes, as described above.

Turning now to the blood separation chamber 26, it may be variously constructed, with FIG. 4 showing a representative embodiment. Further details of a separation chamber 26 of the type shown in FIG. 4 and its operation may be found in U.S. Pat. No. 5,316,667.

Preferably, the chamber 26 is formed of a pair of flexible, deformable sheets of material (e.g., a polyvinyl chloride material) that are sealed together at their perimeter. One of the sheets defines a high-G (outer) wall 90 when the chamber 26 is mounted into the centrifuge 14, while the other sheet defines a low-G (inner) wall 92 that is positioned closer to the rotational axis of the centrifuge 14. A plurality of ports 30, 32, 34, 36, and 38 may extend through the sealed perimeter to allow fluid flow between the interior of the chamber 26 and the other components of the flow circuit 12. In the illustrated embodiment, the ports 30, 32, 34, 36, and 38 are arranged side-by-side along the top edge of the chamber 26, but it is also within the scope of the present disclosure for different ports to be associated with different edges of the chamber and/or for one or more of the ports to extend through one of the walls of the chamber. It is also within the scope of the present disclosure for a different number of ports to be associated with the chamber.

Figure 6:
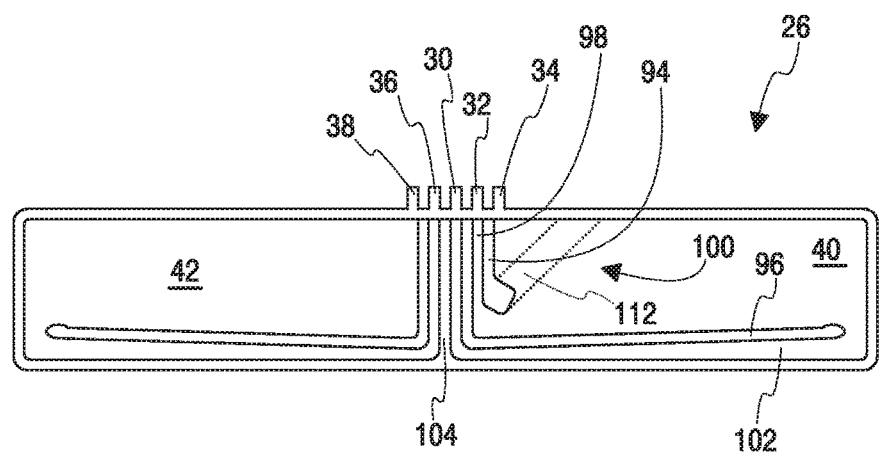
FIG. 6 is a plan view of the blood separation chamber shown in FIG. 5, out of association with the spool.

The chamber 26 may further include a plurality of interior seals that define first and second chambers 40 and 42 and direct the flow of separated blood components within the chamber 26. As shown in FIGS. 5 and 6, there are three ports 30, 32, and 34 associated with the first stage 40 of the illustrated chamber 26. Depending on the particular blood processing procedure, the ports may have different functionality but, in a therapeutic platelet depletion procedure, the port identified at 32 is used for conveying blood from a blood source into the first stage 40. During such a therapeutic platelet depletion procedure, the other two ports 30 and 34 serve as outlet ports for separated blood components exiting the first stage 40. More particularly, the first outlet port 34 conveys a low density blood component from the first stage 40, while the second outlet port 30 conveys a high density blood component from the first stage 40.

One of the separated blood components is transferred from the first stage 40 to the second stage 42 via tubing and a port 38 associated with the second stage 42. The component transferred to the second stage 42 is further fractionated into sub-components, with one of the sub-components being removed from the second stage 42 via an outlet port 36 and the other sub-component remaining and accumulating in the second stage 42.

Blood Separation and Interface Monitoring and Control

In one method of therapeutic platelet depletion, blood enters the first stage 40 of the separation chamber 26 via the inlet port 32 and is separated into red blood cells (i.e., the high density blood component) and platelet-rich plasma (i.e., the low density blood component). The red blood cells are returned to the blood source via the outlet port 30, while the platelet-rich plasma is conveyed out of the first stage 40 via the outlet port 34 and into the second stage 42 via the inlet port 38. In the second stage 42, the platelet-rich plasma is separated into platelet-poor plasma and platelets or platelet concentrate. The platelet-poor plasma is removed from the second stage 42 and may be returned to the blood source via the outlet port 36, leaving the platelets/platelet concentrate to accumulate in the second stage 42 for eventual transfer to a waste container 86, as will be described in greater detail herein.

As FIG. 6 shows, a first interior seal 94 is located between the low density outlet port 34 and the blood inlet port 32. A second interior seal 96 is located between the high density outlet port 30 and the blood inlet port 32. The interior seals 94 and 96 form a fluid passage 98 (a blood inlet in a therapeutic platelet depletion procedure) and a low density collection region 100 in the first stage 40. The second interior seal 96 also forms a portion of a fluid passage 102 (an outlet for high density blood components in a therapeutic platelet depletion procedure) in combination with the internal seal 104 that divides the first and second stages 40 and 42.

Figure 7:
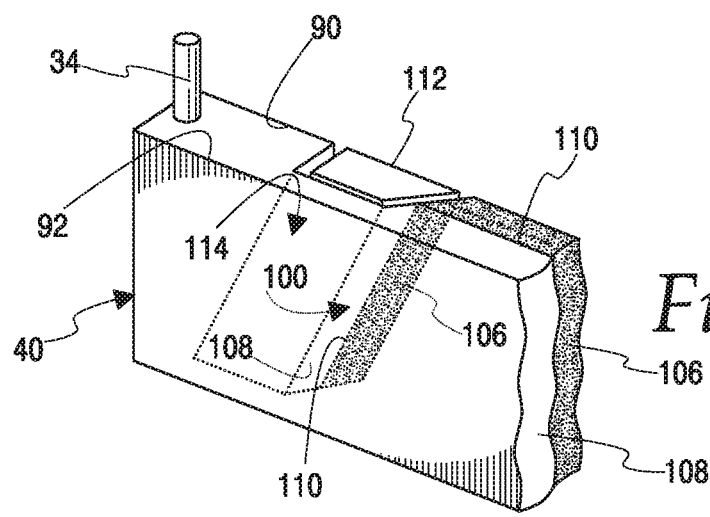
FIG. 7 is an enlarged perspective view of an interface ramp carried by the centrifuge in association with the blood separation chamber, showing the centrifugally separated red blood cell layer and platelet-rich plasma layer within the chamber when in a desired location on the ramp.

In a therapeutic platelet depletion procedure, the fluid passage 98 channels blood directly into the circumferential flow path immediately next to the low density collection region 100. As shown in FIG. 7, the blood separates into an optically dense layer 106, which forms as cellular components move under the influence of centrifugal force toward the high-G (outer) wall 90 of the chamber 26. The optically dense layer 106 will include red blood cells (and, hence, will be referred to herein as the "RBC layer") but, depending on the speed at which the centrifuge 14 is spun, other cellular components (e.g., larger white blood cells and platelets) may also be present in the RBC layer 106.

The movement of the component(s) of the RBC layer 106 displaces less dense blood components radially toward the low-G (inner) wall 92 of the chamber 26, forming a second, less optically dense layer 108. The less optically dense layer 108 includes plasma and platelets (and, hence, will be referred to herein as the "PRP layer") but, depending on the speed at which the centrifuge 14 is rotated and the length of time that the blood is resident in the centrifuge 14, other components (e.g., smaller white blood cells) may also be present in the PRP layer 108.

Figure 8:
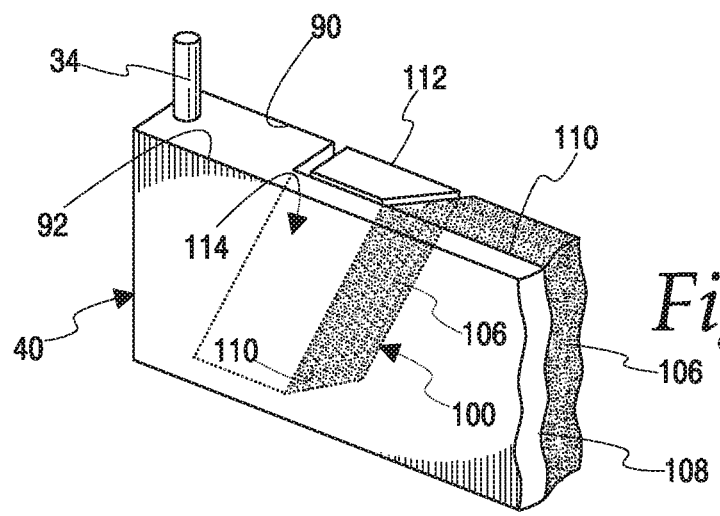
FIG. 8 is an enlarged perspective view of the interface ramp shown in FIG. 7, showing an interface between the red blood cell and platelet-rich plasma layers at an undesired high location on the ramp.
Figure 9:
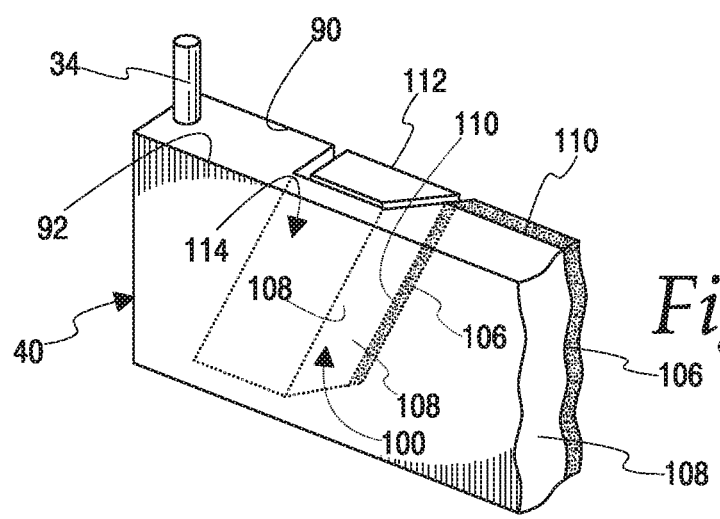
FIG. 9 is an enlarged perspective view of the interface ramp shown in FIG. 7, showing the interface between the red blood cell and platelet-rich plasma layers at an undesired low location on the ramp.

The transition between the RBC and PRP layers 106 and 108 is generally referred to as the interface 110 (FIG. 7). The location of the interface 110 within the chamber 26 can dynamically shift during blood processing, as shown in FIGS. 8 and 9. If the location of the interface 110 is too high (that is, if it is too close to the low-G wall 92 and the outlet port 34, as FIG. 8 shows), red blood cells can spill over and into the low density collection region 100, adversely affecting the quality of the platelet-rich plasma. On the other hand, if the location of the interface 110 is too low (that is, if it resides too far away from the low-G wall 92, as FIG. 9 shows), the collection efficiency of the device 10 may be impaired.

As FIG. 7 shows, a ramp 112 may extend radially inwardly from the bowl 16 of the centrifuge 14 at an angle across the low density collection region 100. The angle, measured with respect to the axis of the outlet port 34 (or the rotational axis) is about 30° in one embodiment. FIG. 7 shows the orientation of the ramp 112 when viewed from the low-G wall 92 of the chamber 26 (or from the spool 18). FIG. 6 shows, in phantom lines, the orientation of the ramp 112 when viewed from the high-G wall 90 of the chamber 26 (or from the bowl 16). Further details of the angled relationship of the ramp 112 and the outlet port 34 can be found in U.S. Pat. No. 5,632,893, which is hereby incorporated herein by reference.

The ramp 112 forms a tapered wedge that restricts the flow of fluid toward the outlet port 34. The top edge of the ramp 112 extends to form a constricted passage 114 along the low-G wall 92. The PRP layer 108 must flow through the constricted passage 114 to reach the outlet port 34.

Figure 10:
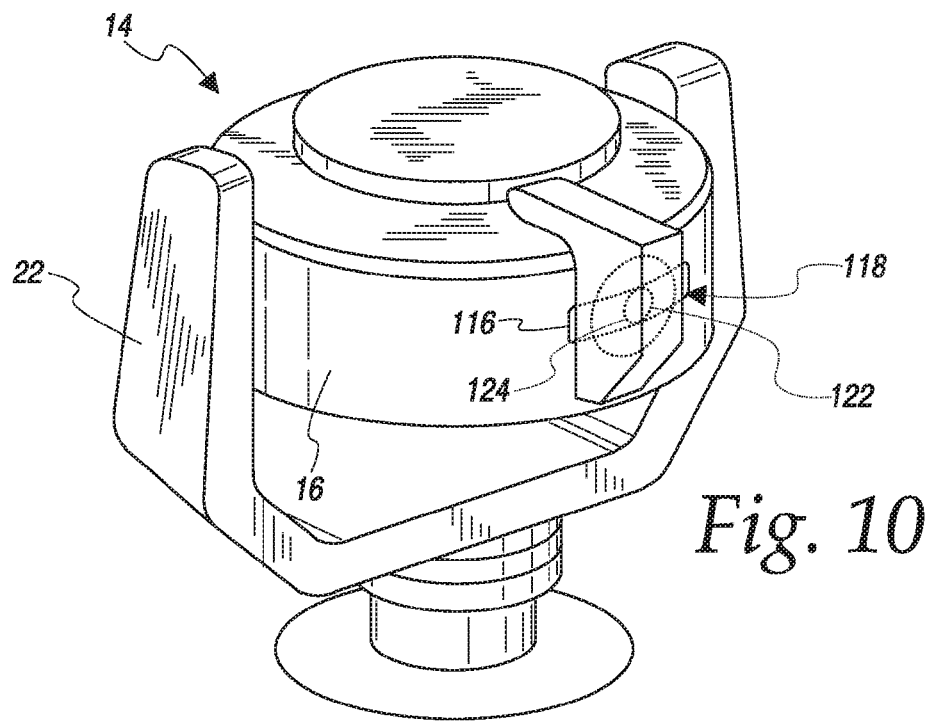
FIG. 10 is a perspective view of the bowl and spool of the centrifuge when in the operating position, showing one embodiment of an interface sensor assembly being carried by the centrifuge to view the interface ramp during rotation of the bowl.

As FIG. 7 shows, the ramp 112 makes the interface 110 between the RBC layer 106 and the PRP layer 108 more discernible for detection, displaying the RBC layer 106, PRP layer 108, and interface 110 for viewing through the high-G wall 90 of the chamber 26. The bowl 16 may include a light-transmissive portion or window 116 (FIGS. 10 and 11) at least partially aligned with the ramp 112 to allow for optical monitoring of the ramp 112 from a position outside of the bowl 16.

Figure 11:
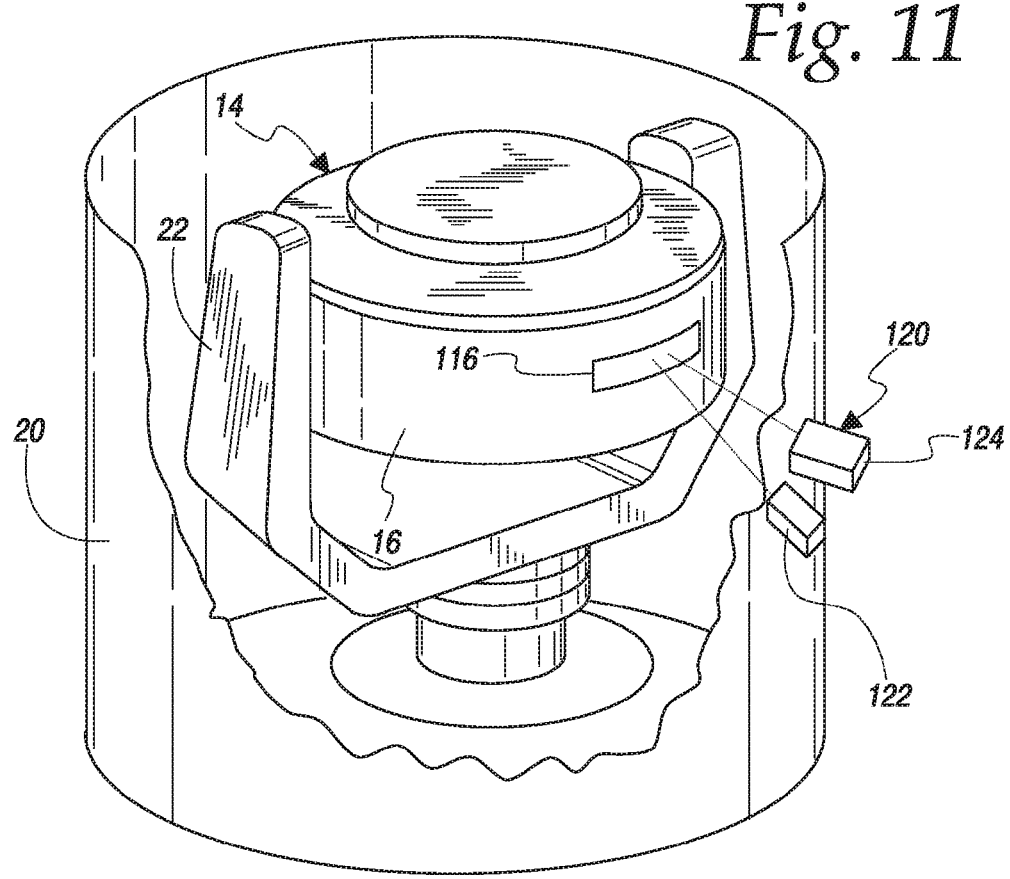
FIG. 11 is a perspective view of another embodiment of an interface sensor assembly, which is mounted to a stationary location to view the interface ramp during rotation of the bowl.

In one embodiment, the blood separation device 10 includes a viewing head or interface sensor assembly 118 carried on the yoke 22 (FIG. 10) to optically view the transition in optical density between the RBC layer 106 and the PRP layer 108 on the ramp 112. In such an embodiment (which is described in greater detail in U.S. Pat. No. 5,980,757, which is hereby incorporated herein by reference), the interface sensor assembly 118 rotates with the yoke 22 during a procedure while monitoring the ramp 112 through the window 116 of the bowl 16. In another embodiment, an interface sensor assembly 120 is mounted to the enclosure or bucket 20 or otherwise positioned outside of the bucket 20 (FIG. 11). In such an embodiment (which is described in greater detail in U.S. Patent Application Publication No. 2014/0045668), the interface sensor assembly 120 is stationary during a procedure while monitoring the ramp 112 through the window 116 of the bowl 16. The interface sensor assembly 118, 120 is functional to determine the location of the interface 110 on the ramp 112 and, if the interface 110 is located at an improper location (e.g., in the locations of FIG. 8 or 9), to cooperate with the system controller to correct the location of the interface 110.

In either embodiment, the interface sensor assembly 118, 120 includes a light source 122, which emits light that is absorbed by red blood cells, such as a red light. The interface sensor assembly 118, 120 also includes a light detector 124, which may be mounted adjacent to the light source 122 or at any other suitable light-receiving location.

The interface ramp 112 is formed of a light-transmissive material. The light from the light source 122 will thereby pass through the window 116 of the bowl 16 and the ramp 112 every time the rotating bowl 16 and interface sensor assembly 118, 120 align. The spool 18 may carry a light reflective material behind the interface ramp 112 to enhance its reflective properties. The spool 18 reflects incoming light received from the light source 122 out through the window 116 of the bowl 16, where it is received by the light detector 124.

As the window 116 of the bowl 16 comes into alignment with the interface sensor assembly 118, 120, the light detector 124 will first sense light reflected through the PRP layer 108 on the ramp 112. Eventually, the RBC layer 106 adjacent the interface 110 on the ramp 112 will enter the optical path of the interface sensor assembly 118, 120. The RBC layer 106 absorbs light from the light source 122 and thereby reduces the previously sensed intensity of the reflected light. The amount of time that a greater intensity of the reflected light is sensed by the light detector 124 (i.e., the pulse width) represents the amount of light from the light source 122 that is transmitted through the PRP layer 108 as the ramp 112 rotates through the path of light from the light source 122. With this information, a processing element or module of the controller of the blood separation device 10 can determine the location of the interface 110 on the ramp 112 relative to the constricted passage 114. A more detailed discussion of exemplary algorithms by which the controller may receive and process signals from the interface sensor assembly 118, 120 to determine the location of the interface 110 on the ramp 112 may be found in U.S. Pat. No. 6,312,607, which is hereby incorporated herein by reference.

When the location of the interface 110 on the ramp 112 has been determined, the processing element outputs that information to an interface command element or module of the controller, which may include a comparator to compare the interface location output with a desired interface location and generate an error signal. The error signal may take a number of forms but, in one embodiment, is expressed in terms of a targeted red blood cell percentage value (i.e., the percentage of the ramp 112 which should be occupied by the RBC layer 106).

When the control value is expressed in terms of a targeted red blood cell percentage value, a positive error signal indicates that the RBC layer 106 on the ramp 112 is too large (as FIG. 8 shows). The controller generates a signal to adjust an operational parameter accordingly, such as by reducing the rate at which platelet-rich plasma is removed through the outlet port 34. The interface 110 moves away from the constricted passage 114 toward the desired control position (as FIG. 7 shows), where the error signal is zero.

A negative error signal indicates that the RBC layer 106 on the ramp 112 is too small (as FIG. 9 shows). The controller generates a signal to adjust an operational parameter accordingly, such as by increasing the rate at which platelet-rich plasma is removed through the outlet port 34. The interface 110 moves toward the constricted passage 114 to the desired control position (FIG. 7), where the error signal is again zero.

It should be understood that this is merely one possible approach to monitoring and controlling the location of an interface between separated blood components within the first stage 40 of the chamber 26. Other approaches to interface monitoring and control may be employed without departing from the scope of the present disclosure.

Pre-Processing

Turning now to an exemplary platelet depletion procedure, it may begin with an operator selecting (e.g., using the user interface screen 62) the procedure from among the variety of procedures that the device 10 is capable of performing. The operator may enter a variety of information requested by the system controller that allows the controller to better carry out the procedure. For example, in one embodiment, it may be advantageous for the controller to be provided with the total blood volume of the blood source (which will be referred to herein as TBV), a platelet precount or the initial platelet concentration of the blood of the blood source (which will be referred to herein as $Plt_{pre}$), and a platelet post-count or a target platelet concentration to be achieved for the blood of the blood source by the end of the procedure (which will be referred to herein as $Plt_{post}$). Other and/or additional information (e.g., the total amount of blood to be processed) may also be provided to the system controller without departing from the scope of the present disclosure.

In addition to performing preliminary system status checks (e.g., ensuring that the proper flow circuit 12 has been mounted to the device 10 and that there are no leaks or defects in the flow circuit 12), the controller may calculate a variety of parameters to be used during the procedure. For example, if the total amount of blood to be processed (which may be in the range of 1.5 to 2.0 TBVs in one embodiment) is not selected by the operator, then the controller may calculate the total amount of blood to be processed to achieve the selected platelet post-count $Plt_{post}$. In one embodiment, the total amount of anticoagulated whole blood to be processed (which will be referred to herein as $WB_{total\ processed\ (+AC)}$) is calculated using the following equation:

$$WB_{total\ processed(+AC)}(\text{mL}) = -\ln\left(\frac{Plt_{post}}{Plt_{pre}}\right) \times \frac{TBV}{CE}, \quad (1)$$

where

CE is the platelet collection efficiency of the blood separation device 10.

Variations of Equation 1 may also be used by the system controller. For example, if the blood source is a human, then $WB_{total\ processed\ (+AC)}$ may be calculated using an equation that accounts for splenic mobilization by predicting the amount of platelets that will be introduced into the blood from the spleen of the blood source during the platelet depletion procedure. An exemplary approach to quantifying a splenic mobilization factor is described in U.S. Pat. No. 5,759,413, which is hereby incorporated herein by reference.

Figure 12:
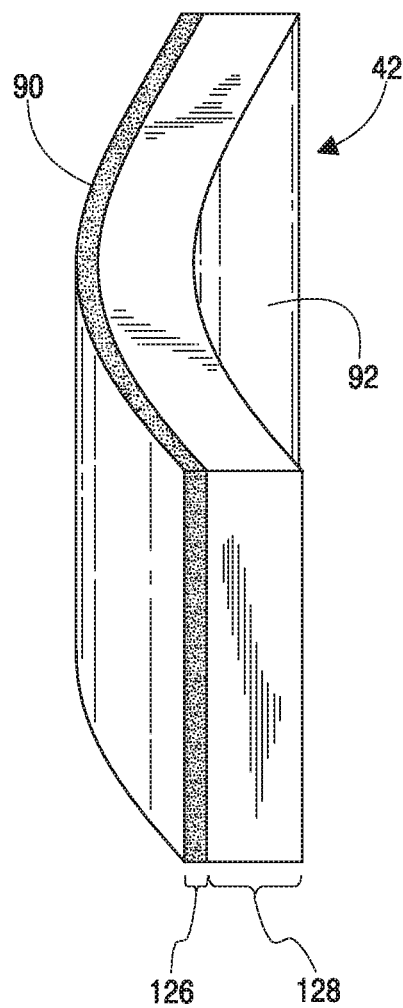
FIG. 12 is an enlarged perspective view of the position of platelets/platelet concentrate and platelet-poor plasma in a second stage of the blood separation chamber during a conventional procedure.
Figure 13:
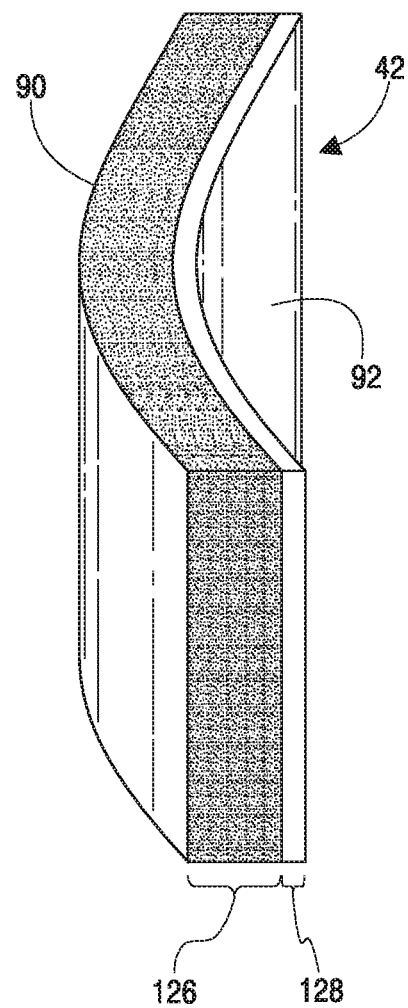
FIG. 13 is an enlarged perspective view of the position of platelets/platelet concentrate and platelet-poor plasma in a second stage of the blood separation chamber at the end of a platelet accumulation phase of a cycle of a platelet depletion procedure according to the present disclosure.

As will be described, the platelet depletion procedure may be a batch process in which a cycle of accumulating platelets/platelet concentrate in the separation chamber 26 and then flushing the platelets/platelet concentrate to a waste container 86 is repeated, in which case the controller may also calculate the amount of blood to be processed during each cycle. The amount of platelets/platelet concentrate to be accumulated during each cycle will depend on a variety of factors, including the size and configuration of the chamber 26 (particularly, the second stage 42 of the chamber 26). However, regardless of the exact amount of platelets/platelet concentrate that is accumulated in the second stage 42 during each cycle, the percentage of the volume of the second stage 42 that is occupied by the platelets/platelet concentrate at the end of the platelet accumulation phase of each cycle is significantly greater than the percentage occupied by the platelets/platelet concentrate in a conventional procedure (e.g., a conventional platelet collection procedure). For example, FIGS. 12 and 13 compare the amounts of platelets/platelet concentrate 126 and platelet poor plasma 128 present in the second stage 42 of the chamber 26 during a conventional procedure (FIG. 12) and at the end of the platelet accumulation phase of a cycle of a platelet depletion procedure of the type described herein (FIG. 13). As shown, the majority of the volume of the second stage 42 is occupied by platelet poor plasma 128 during the conventional procedure (FIG. 12), whereas the majority of the volume of the second stage 42 is occupied by platelets/platelet concentrate 126 at the end of the platelet accumulation phase of a cycle of a platelet depletion procedure according to the present disclosure (FIG. 13).

The per-cycle amount of blood to be processed (which will be referred to herein as $WB_{per\ cycle\ (+AC)}$) may be calculated according to any suitable approach, but in one embodiment is calculated using the following equation:

$$WB_{per\ cycle(+AC)}(\text{mL}) = \frac{-TBV}{CE} \times \ln\left(1 - \frac{\text{Max Capacity of Plts}}{TBV * Plt_{cycle}}\right) \times \left(1 + \frac{1\ \text{part}\ AC}{X\ \text{parts}\ WB}\right), \quad (2)$$

where

Max Capacity of Plts is the maximum chamber capacity of platelets/platelet concentrate to be accumulated in the second stage 42 of the blood separation chamber 26, $Plt_{cycle}$ is the platelet concentration of the blood at the beginning of the cycle, and $$\frac{1\ \text{part}\ AC}{X\ \text{parts}\ WB}$$

is the ratio of anticoagulant to blood of the anticoagulated whole blood to be conveyed into the first stage 40 of the blood separation chamber 26.

Typically, all of the factors of Equation 2 will remain constant for each cycle of a procedure except for $Plt_{cycle}$. As the procedure continues, platelets are removed from the blood of the blood source, while other blood components (e.g., red blood cells and plasma) and replacement fluid (e.g., saline) may be conveyed to the blood source, thereby continuously decreasing the platelet concentration of the blood of the blood source. As $Plt_{cycle}$ will be different for each cycle, it may be advantageous for the controller to calculate $WB_{per\ cycle\ (+AC)}$ at the beginning of the procedure (for the initial cycle) and then again between each consecutive cycle. Alternatively, $WB_{per\ cycle\ (+AC)}$ for each cycle (which will be different for each cycle) may be calculated at the beginning of the procedure, which will also determine the number of cycles that must be executed to reach $WB_{total\ processed\ (+AC)}$ by the end of the final cycle.

In general, as the concentration of platelets in the blood decreases, more blood must be processed to accumulate a given amount of platelets/platelet concentrate in the second stage 42 of the chamber 26, such that $WB_{per\ cycle\ (+AC)}$ will tend to increase for each successive cycle. However, it will often be the case that the difference between $WB_{total\ processed\ (+AC)}$ and the amount of blood that has been processed leading up to the final cycle is less than the $WB_{per\ cycle\ (+AC)}$ calculated for the final cycle. In this case, less blood will actually be processed during the final cycle (which will be an amount equal to the difference between $WB_{total\ processed\ (+AC)}$ and the amount of blood that has been processed leading up to the final cycle) than the $WB_{per\ cycle\ (+AC)}$ that is calculated for the final cycle. If the amount of blood processed during the final cycle is less than the calculated $WB_{per\ cycle\ (+AC)}$ value, then that amount may be greater than, equal to, or less than the amount of blood processed during the preceding cycle. This may also be true when there is no specified $WB_{total\ processed\ (+AC)}$, but instead a particular $Plt_{post}$ to be achieved, with less blood needing to be processed during the final cycle to achieve $Plt_{post}$ than a calculated $WB_{per\ cycle\ (+AC)}$ value that would be required to accumulate the same amount of platelets/platelet concentrate in the second stage 42 as in each of the preceding cycles. Alternatively, rather than carrying out a final cycle during which a lesser amount of platelets/platelet concentrate is accumulated in the second stage 42 than the amount of platelets/platelet concentrate accumulated in the second stage 42 during each of the preceding cycles, it is also within the scope of the present disclosure for the controller to execute a final cycle involving the processing of the amount of blood required to accumulate the same amount of platelets/platelet concentrate in the second stage 42 as in each of the preceding cycles, regardless of the calculated $WB_{per\ cycle\ (+AC)}$ value.

Platelet Depletion Procedure

When the system controller has received all of the necessary input, performed the necessary preliminary calculations and status checks (e.g., to confirm that the flow circuit 12 is properly installed and that the various components of the device 10 are functioning properly), and primed the flow circuit 12, the first cycle of the platelet depletion procedure may begin.

The system controller instructs one or more of the pumps 56 to draw blood from the blood source into the flow circuit 12 via one of the blood source access devices 64. One or more of the pumps 56 may be actuated to draw anticoagulant into the flow circuit 12 to be mixed with the blood as it is drawn to and through one or more of the cassettes 50A, 50B, 50C.

Figure 14:
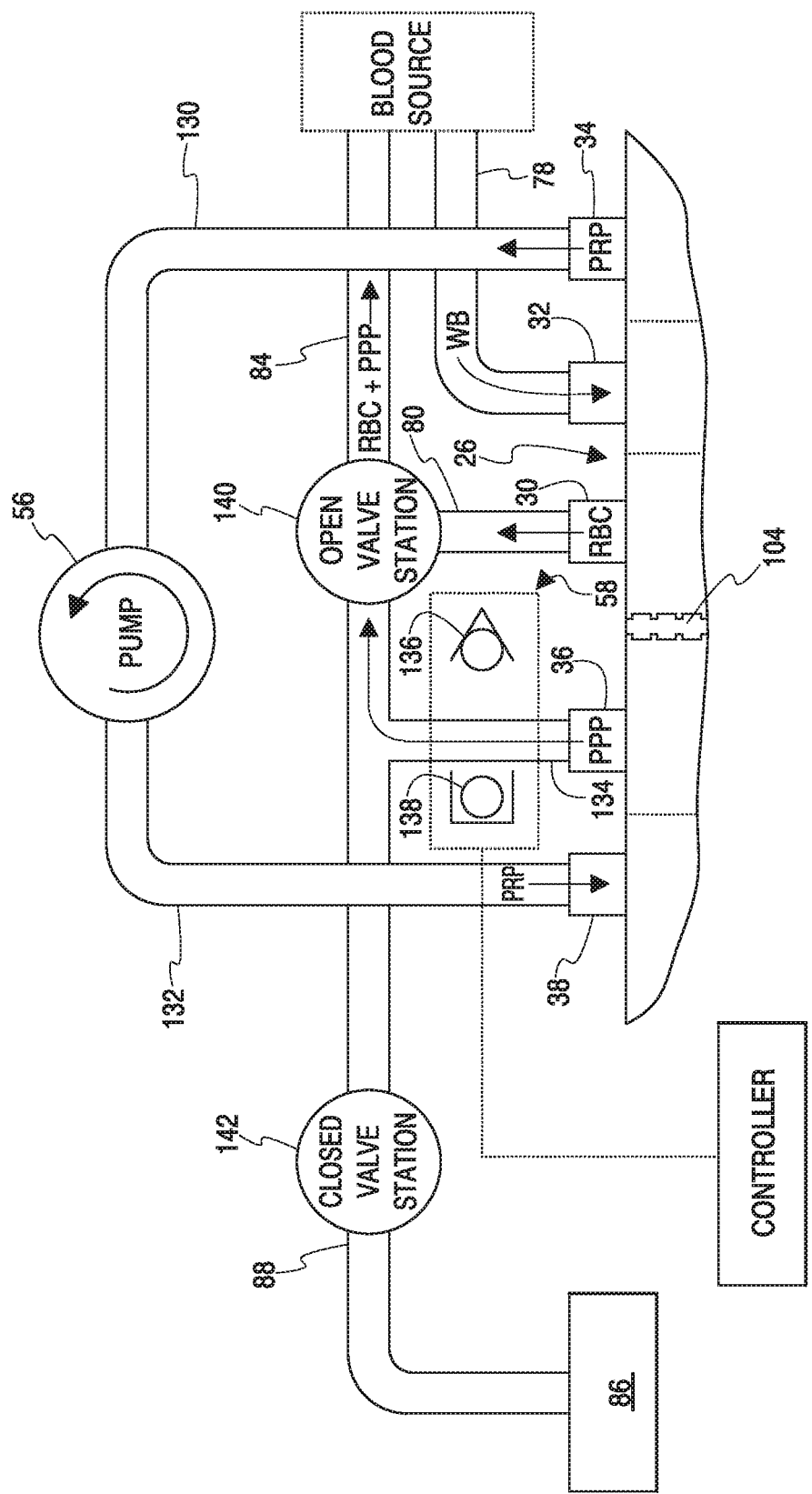
FIG. 14 is a schematic view of portions of the blood separation device and of the fluid flow circuit during a platelet accumulation phase.

The valve stations of the cassettes 50A, 50B, 50C are actuated, as necessary, to direct the anticoagulated blood through the tubing 78 connected to the whole blood inlet port 32 associated with the first stage 40 of the separation chamber 26. FIG. 14 illustrates a simplified, schematic version of the way in which blood and its constituents are directed into and out of the separation chamber 26 during this platelet accumulation phase of the cycle.

The centrifuge 14 rotates the blood separation chamber 26 about a rotational axis at a speed that is sufficient to separate the blood in the first stage 40 into the RBC layer 106 and the PRP layer 108. The RBC layer 106 moves toward the high-G wall 90 of the chamber 26, where it flows out of the first stage 40 via the outlet port 30. Tubing 80 connected to the outlet port 30 may direct the RBC layer 106 to one of the cassettes (e.g., the middle cassette 50B), with the valve stations of the cassette being operated to direct the RBC layer 106 back to the blood source via one of the blood source access devices 66. In one embodiment, the RBC layer 106 is directed from one cassette (which may be the middle cassette 50A) to another cassette (which may be the left cassette 50A) before the RBC layer 106 is returned to the blood source. It is also within the scope of the present disclosure for the RBC layer 106 (or at least a portion thereof) to be directed to some other location (e.g., to a waste container or to a storage container).

While the RBC layer 106 is conveyed out of the first stage 40 via the outlet port 30, the PRP layer 108 is conveyed out of the first stage 40 via the other outlet port 34 associated with the first stage 40. The PRP layer 108 travels through tubing 130 associated with the outlet port 34 and is directed to the inlet port 38 of the second stage 42 of the chamber 26 via tubing 132 (FIG. 14). The PRP layer 108 may be conveyed to one of the cassettes (which may be the right cassette 50C in one embodiment), which directs the PRP layer 108 to the tubing 132 connected to the inlet port 38 of the second stage 42 of the chamber 26, or it may instead travel from the first stage 40 to the second stage 42 without passing through a cassette.

The same rotation that separates blood in the first stage 40 into the RBC layer 106 and the PRP layer 108 separates the PRP layer 108 in the second stage 42 into platelets/platelet concentrate 126 and platelet-poor plasma 128. The platelet-poor plasma 128 is conveyed out of the second stage 42 via the outlet port 36, with tubing 134 directing the platelet-poor plasma 128 from the outlet port 36 to a cassette (which may be the right cassette 50C in one embodiment). The platelet-poor plasma 128 may then be conveyed back to the blood source, which may include passing the platelet-poor plasma to a second cassette (e.g., the left cassette 50A), where it mixes with the RBC layer 106 also being returned to the blood source. It is also within the scope of the present disclosure for the platelet-poor plasma 128 to be mixed with the RBC layer 106 at some other location within the fluid flow circuit 12 or for the platelet-poor plasma 128 to be returned to the blood source without being mixed with the RBC layer 106. It is additionally within the scope of the present disclosure for all or a portion of the platelet-poor plasma 128 to be directed to some other location (e.g., to a waste container or a storage container) rather than being returned to the blood source.

While the blood is being separated into the RBC layer 106 and the PRP layer 108 in the first stage 40 and the platelet-poor plasma 128 is being conveyed out of the second stage 42, the platelets/platelet concentrate 126 accumulates in the second stage 42 until the maximum chamber capacity of platelets/platelet concentrate 126 is reached. According to one embodiment, this is determined by the $WB_{per\ cycle\ (+AC)}$ value calculated by the system controller. When the controller has been determined that the calculated amount of whole blood has been drawn into and processed within the chamber 26, then the controller will consider the amount of platelets/platelet concentrate 126 in the second stage 42 to have reached the maximum chamber capacity.

Figure 15:
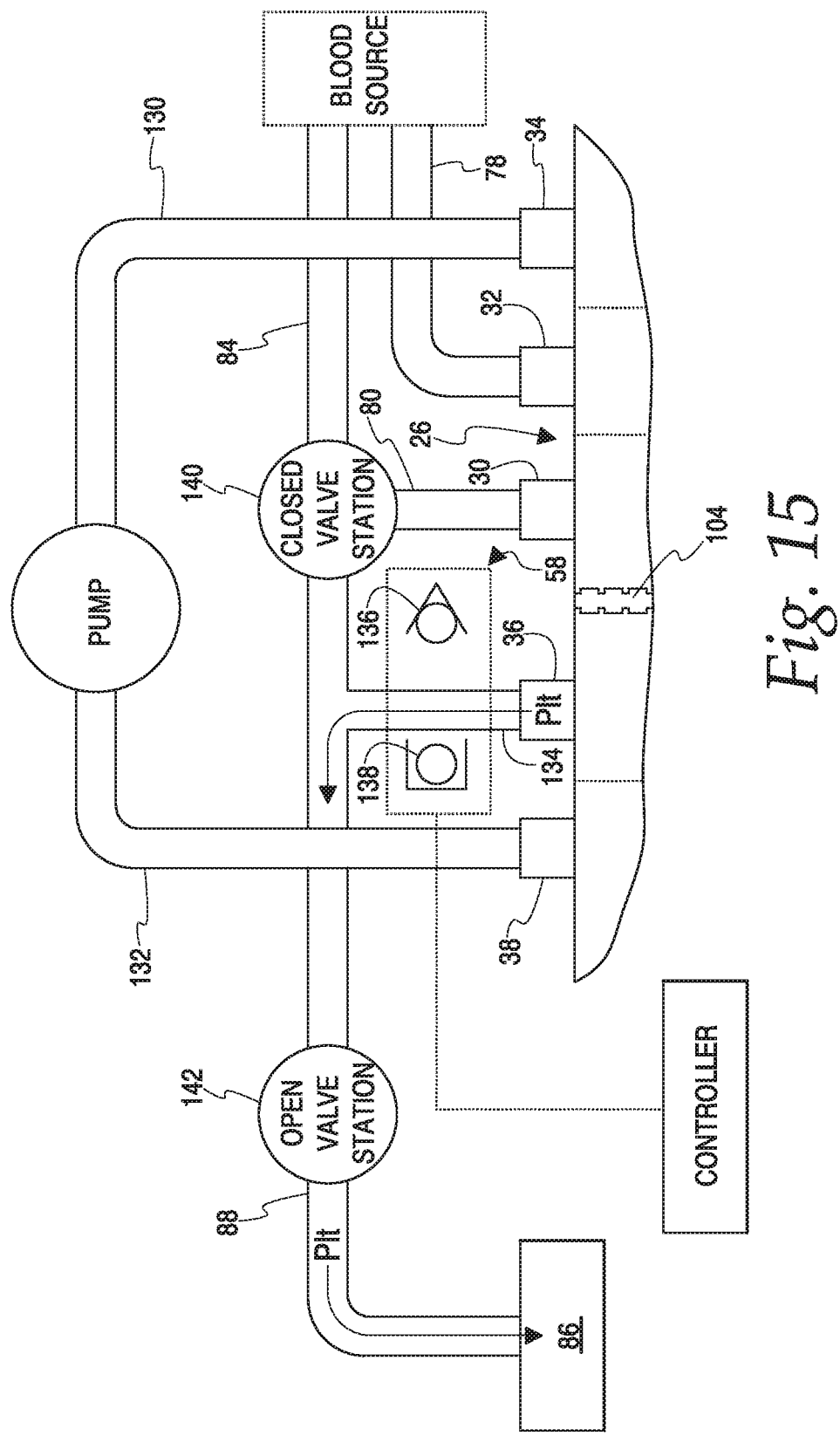
FIG. 15 is a schematic view of portions of the blood separation device and of the fluid flow circuit during a platelet flush phase.

According to another embodiment, optical monitoring techniques may be employed to determine when the amount of platelets/platelet concentrate 126 in the second stage 42 has reached the maximum chamber capacity. As shown in FIGS. 14 and 15, the tubing 134 connected to the outlet port 36 of the second stage 42 may pass through the optical line monitor 58 of the device 10. When the system is so configured, the optical line monitor 58 may be used to determine when the maximum chamber capacity of platelets/platelet concentrate has been accumulated in the second stage 42 by monitoring the optical density of fluid flowing through the tubing 134. This may be used instead of the $WB_{per\ cycle\ (+AC)}$ calculation to determine when to end the platelet accumulation phase of the cycle or may be employed in combination with the $WB_{per\ cycle\ (+AC)}$ calculation to determine when to end the platelet accumulation phase of the cycle.

In embodiments in which the tubing 134 connected to the outlet port 36 of the second stage 42 passes through the optical line monitor 58, a light source 136 of the optical line monitor 58 may emit a light into the tubing 134 and the fluid passing through the tubing 134. The light may be of any wavelength that is transmitted through platelet-poor plasma 128 to a different degree than through platelets/platelet concentrate 126 but, in one embodiment, comprises red light. The tubing 134 may be positioned between the light source 136 and a light detector 138 of the optical line monitor 58, which receives at least a portion of the light from the light source 136 that has passed through the tubing 134 and the fluid flowing therethrough. A more detailed discussion of an exemplary optical line monitor 58 can be found in U.S. Pat. No. 6,312,607.

The light detector 138 transmits a signal to the system controller, which may be representative of the amount of light or the nature of the light that is being received by the light detector 138, such that the nature of the signal differs when the light detector 138 receives different amounts (or types) of light from the light source 136. In one embodiment, the magnitude of the signal from the light detector 138 to the controller is proportional to the amount of light received by the light detector 138, such that the magnitude of the signal will decrease when less light is transmitted through the tubing 134 and the fluid flowing therethrough. Typically, less light will pass through platelets/platelet concentrate 126 than platelet-poor plasma 128, in which case the magnitude of the signal received by the controller will decrease when platelets/platelet concentrate 126 begins appearing in the tubing 134 connected to the outlet port 36 of the second stage 42.

The presence of platelets/platelet concentrate 126 in the tubing 134 connected to the outlet port 36 of the second stage 42 indicates that the maximum chamber capacity of platelets/platelet concentrate 126 has been reached. At this time, the controller may end the platelet accumulation phase of the cycle. In one embodiment, the controller may instruct the pump or pumps 56 drawing fluid out of the second stage 42 to temporarily reverse operation, thereby returning the platelets/platelet concentrate 126 in the tubing 134 to the second stage 42 before moving to the next phase.

With the maximum chamber capacity of platelets/platelet concentrate 126 in the second stage 42, the controller ends the first cycle by ordering the centrifuge 14 to temporarily stop rotation of the chamber 26 and commanding at least one of the pumps 56 to operate to convey the accumulated platelets/platelet concentrate 126 out of the second stage 42 (FIG. 15). In one embodiment, the chamber 26 may be removed from the centrifuge 14 by the operator before the platelets/platelet concentrate 126 is conveyed out of the second stage 42 to re-suspend the platelets/platelet concentrate 126. This may be done by manually manipulating the second stage 42 of the chamber 26 or otherwise manipulating the second stage 42 to mix the platelets/platelet concentrate 126 accumulated therein, which may include mounting the chamber 26 to a resuspension apparatus, such as one of the type described in U.S. Patent Application Publication No. 2014/0043930, which is hereby incorporated herein by reference. However, it is also within the scope of the present disclosure for the platelets/platelet concentrate 126 to be conveyed out of the second stage 42 of the chamber 26 without being resuspended.

The device 10 may convey the platelets/platelet concentrate 126 out of the second stage 42 by directing fluid through the second stage 42, which flushes the platelets/platelet concentrate 126 out of the second stage 42 via the outlet port 36. The nature of the fluid may vary without departing from the scope of the present disclosure, but may be saline or anticoagulant. In another embodiment, at least a portion of the platelet-poor plasma 128 conveyed out of the second stage 42 is temporarily stored rather than being returned to the blood source. This stored platelet-poor plasma 128 may be pumped through the second stage 42 to flush the accumulated platelets/platelet concentrate 126 out of the second stage 42 via the outlet port 36. The platelets/platelet concentrate 126 may be directed out of the second stage 42 to a waste container 86 via one of the cassettes (which may be the right cassette 50C in one embodiment). A comparison between FIGS. 14 and 15 shows how the valve stations 140 and 142 (which may belong to the same cassette or different cassettes) may be manipulated to direct the fluid flowing out of the second stage outlet port 36 toward the blood source during the platelet accumulation phase (FIG. 14, in which one valve station 140 is open and the other 142 is closed) or toward a waste container 86 during the platelet flush phase (FIG. 15, in which the first valve station 140 is closed and the other 142 is open).

When the accumulated platelets/platelet concentrate 126 has been conveyed out of the second stage 42, the centrifuge 14 may begin rotating the chamber 26 again and a second cycle may begin. The second cycle may be substantially identical to the first cycle, except that more blood must typically be processed to accumulate the same amount of platelets/platelet concentrate 126 in the second stage 42, as described above. The phases of platelet accumulation and platelet flush alternate until the controller determines that there is only one final cycle required to complete the procedure (e.g., by processing the calculated total amount of blood or decreasing the platelet concentration of the blood to a target value). The final cycle may proceed in the same way as the preceding cycles, but rather than accumulating the same amount of platelets/platelet concentrate 126 in the second stage 42 as in each of the preceding cycles, a smaller amount of platelets/platelet concentrate 126 may be accumulated therein, as necessary to achieve the target total amount of processed blood or the target platelet concentration. Alternatively, as described above, it is also within the scope of the present disclosure to accumulate the same amount of platelets/platelet concentrate 126 in the second stage 42 during the final cycle as during each of the preceding cycles, regardless of the calculated $WB_{per\ cycle\ (+AC)}$. Additionally, the final cycle may differ from the preceding cycles in that it is not necessary to remove the accumulated platelets/platelet concentrate 126 from the second stage 42 of the chamber 26 at the end of the procedure, as the entire fluid flow circuit 12 may be disposed of with the platelets/platelet concentrate 126 remaining in the chamber 26. Hence, the final cycle may include a platelet accumulation phase without also including a platelet flush phase.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of depleting platelets from blood from a blood source, comprising:
   (a) executing a cycle comprising
      conveying blood into a first stage of a blood separation chamber,
      separating the blood in the first stage of the blood separation chamber into platelet-rich plasma and red blood cells,
      conveying at least a portion of the platelet-rich plasma into a second stage of the blood separation chamber,
      separating said at least a portion of the platelet-rich plasma in the second stage of the blood separation chamber into platelets and platelet-poor plasma, and
      conveying at least a portion of the platelet-poor plasma out of the second stage of the blood separation chamber while allowing the platelets to accumulate in the second stage of the blood separation chamber;
   (b) determining that a maximum chamber capacity of platelets has accumulated in the second stage of the blood separation chamber; and
   (c) ending the cycle by conveying the accumulated platelets out of the second stage of the blood separation chamber, wherein
      said determining that the maximum chamber capacity of platelets has accumulated in the second stage of the blood separation chamber comprises determining that a predetermined cycle amount of blood has been conveyed into the first stage of the blood separation chamber, and
      the predetermined cycle amount of blood to be conveyed into the first stage of the blood separation chamber is calculated using the equation:

$$WB_{per\ cycle(+AC)}(\text{mL}) = \frac{-TBV}{CE} \times \ln\left(1 - \frac{\text{Max Capacity of Plts}}{TBV \times Plt_{cycle}}\right) \times \left(1 + \frac{1\ \text{part}\ AC}{X\ \text{parts}\ WB}\right),$$

wherein
$WB_{per\ cycle\ (+AC)}$ is an amount of anticoagulated whole blood to be conveyed into the first stage of the blood separation chamber during the cycle,
TBV is a total blood volume of the blood source,
CE is a platelet collection efficiency of a blood separation device used in combination with the blood separation chamber to deplete platelets from the blood,
Max Capacity of Plts is the maximum chamber capacity of platelets to be accumulated in the second stage of the blood separation chamber,
$Plt_{cycle}$ is a platelet concentration of the blood at the beginning of the cycle, and $$\frac{1\ \text{part}\ AC}{X\ \text{parts}\ WB}$$

is a ratio of anticoagulant to blood of the anticoagulated whole blood to be conveyed into the first stage of the blood separation chamber.

2. A method of depleting platelets from blood from a blood source, comprising:
   (a) executing a cycle comprising
      conveying blood into a first stage of a blood separation chamber,
      separating the blood in the first stage of the blood separation chamber into platelet-rich plasma and red blood cells,
      conveying at least a portion of the platelet-rich plasma into a second stage of the blood separation chamber,
      separating said at least a portion of the platelet-rich plasma in the second stage of the blood separation chamber into platelets and platelet-poor plasma, and
      conveying at least a portion of the platelet-poor plasma out of the second stage of the blood separation chamber while allowing the platelets to accumulate in the second stage of the blood separation chamber;
   (b) determining that a maximum chamber capacity of platelets has accumulated in the second stage of the blood separation chamber; and
   (c) ending the cycle by conveying the accumulated platelets out of the second stage of the blood separation chamber, further comprising
   repeating (a)-(c) until a target platelet concentration of the blood of the blood source has been achieved, wherein
      said repeating (a)-(c) until the target platelet concentration of the blood of the blood source has been achieved comprises repeating (a)-(c) until a predetermined total amount of blood has been conveyed into the first stage of the blood separation chamber, and
      the predetermined total amount of blood to be conveyed into the first stage of the blood separation chamber is calculated using the equation:

$$WB_{total\ processed(+AC)}(\text{mL}) = -\ln\left(\frac{Plt_{post}}{Plt_{pre}}\right) \times \frac{TBV}{CE},$$

wherein
$WB_{total\ processed\ (+AC)}$ is a total amount of anticoagulated whole blood to be conveyed into the first stage of the blood separation chamber, $Plt_{post}$ is the target platelet concentration of the blood of the blood source to be achieved, $Plt_{pre}$ is an initial platelet concentration of the blood of the blood source, TBV is a total blood volume of the blood source, and CE is a platelet collection efficiency of a blood separation device used in combination with the blood separation chamber to deplete platelets from the blood.

* * * * *